US00RE36397E

United States Patent [19]

Zhang et al.

[11] E Patent Number: Re. 36,397

[45] Reissued Date of Patent: Nov. 16, 1999

[54] INHIBITORS OF POLY(ADP-RIBOSE) SYNTHETASE AND USE THEREOF TO TREAT NMDA NEUROTOXICITY

[75] Inventors: Jie Zhang, Ellicott City; Valina L. Dawson, Baltimore; Ted M. Dawson, Baltimore; Solomon H. Snyder, Baltimore, all of Md.

[73] Assignees: The John Hopkins University, Baltimore, Md.; The United States of America, Washington, D.C.

[21] Appl. No.: 09/219,843

[22] Filed: Dec. 23, 1998

Related U.S. Patent Documents

Reissue of:

[64] Patent No.: 5,587,384
Issued: Dec. 24, 1996
Appl. No.: 08/191,508
Filed: Feb. 4, 1994

[51] Int. Cl.[6] ..... A61K 31/165; A61K 31/47

[52] U.S. Cl. ..... 514/309; 514/617; 514/619

[58] Field of Search ..... 514/309, 617, 514/619

[56] References Cited

U.S. PATENT DOCUMENTS

| | | | |
|---|---|---|---|
| 4,594,415 | 6/1986 | Robins et al. | 536/27 |
| 5,177,075 | 1/1993 | Suto et al. | 514/248 |
| 5,262,564 | 11/1993 | Kun et al. | 562/430 |
| 5,338,851 | 8/1994 | Huff et al. | 546/141 |

FOREIGN PATENT DOCUMENTS 0355750 8/1989 European Pat. Off. .

OTHER PUBLICATIONS

Choi, Dennis, "The Role of Glutamate Neurotoxicity in Hypoxic–Ischemic Neuronal Death", *Ann Rev. Neurosci.,* 13:171–82 (1990).

Choi, Dennis, "Glutamate Neurotoxicity and Diseases of the Nervous System", *Neuron,* 1:623–634 (1988).

Meldrum et al., "Excitatory amino acid neurotoxicity and neurodegenerative disease", *TIPS,* 11:379–387 (1990).

Suto et al., "Dihydroisoquinolinones: the design and synthesis of a new series of potent inhibitors of poly (ADP–ribose) polymerase", *Anti–cancer Drug Design,* 7:107–117 (1991).

Banasik et al., "Specific Inhibitors of Poly(ADP–Ribose)Synthetase and Mono (ADP–Ribosyl) Transferase", *J Biol Chem,* 267:1569–1575 (1992).

Dawson et al., "Mechanisms of Nitric Oxide–Mediated Neurotoxicity in Primary Brain Cultures", *J Neuroscience,* 13:2651–2661 (1993).

Dawson et al., "Nitric Oxide Mediates Glutamate Neurotoxicity in Primary Cortical Cultures", *Proc Natl Acad Sci,* 88:6568–6371 (1991).

Nowicki et al., "Nitric Oxide Mediates Neuronal Death After Focal Cerebral Ischemia in the Mouse", *European J Pharmacology,* 204, 339–340 (1991).

Purnell et al., "Novel inhibitors of Poly (ADP–Ribose) Synthetase", *Biochem J,* 185:775–777 (1980).

Wallis et al., "Neuroprotection Against Nitric Oxide Injury with Inhibitors of ADP–ribosylation", *Neuropharmacology,* 5(3):245–248 (1993).

Zhang et al., "Nitric Oxide Activation of Poly(ADP–Ribose) Synthetase in Neurotoxicity", *Science,* 263:687–689 (1994).

Cosi et al., J. Neuroscience Research, 39(1), 38–46, Sep. 1994.

*Primary Examiner*—Phyllis G. Spivack

[57] ABSTRACT

Inhibitors of poly(ADP-ribose) synthetase can be used to prevent neurotoxicity mediated through N-methyl-D-aspartate (NMDA) receptors. Poly(ADP-ribose) synthetase inhibitors can be used therapeutically in the treatment of vascular stroke and neurodegenerative disorders such as Alzheimer's disease, Parkinson's disease and Huntington's disease.

28 Claims, 4 Drawing Sheets

INHIBITORS OF POLY(ADP-RIBOSE) SYNTHETASE AND USE THEREOF TO TREAT NMDA NEUROTOXICITY

Matter enclosed in heavy brackets [ ] appears in the original patent but forms no part of this reissue specification; matter printed in italics indicates the additions made by reissue.

The U.S. Government has a paid-up license in this invention and the right in limited circumstances to require the patent owner to license others on reasonable terms as provided for by the terms of grants awarded by the National Institutes of Health and the U.S. Public Health Service, including USPHS grants DA-00266, Contract DA-271-90-7408, Research Scientist Award DA-00074, USPHS CIDA NS-01578 and an Intramural Research Training Award from the N.I.H.

FIELD OF THE INVENTION

The invention relates to the use of inhibitors of poly (ADP-ribose) synthetase to prevent NMDA neurotoxicity.

BACKGROUND OF THE INVENTION

Nitric oxide (NO) is a messenger molecule that regulates macrophage killing of tumor cells and bacteria (C. F. Nathan and J. B. Hibbs, Jr., Curr. Opin. Immunol. 3, 65 (1991)), blood vessel relaxation (S. Moncada, R. M. J. Palmer, E. A. Higgs, Pharmacol. Rev. 43, 109 (1991); L. J. Ignarro, Ann. Rev. Pharmacol. Toxicol. 30, 535 (1990)) and also is a neurotransmitter (D. S. Bredt and S. H. Snyder, Neuron 8, 3 (1992)). When formed in high quantities in response to actions of the excitatory neurotransmitter glutamate acting at N-methyl- D-aspartate (NMDA) receptors. NO mediates neuronal killing (V. L. Dawson et al., Proc. Natl. Acad. Sci. U.S.A. 88, 6368 (1991); V. L. Dawson et al., J. Neurosci. 13, 2651 (1993)). Toxicity due to NMDA accounts for neural damage in vascular stroke, as NO synthase (NOS) inhibitors prevent stroke damage (J. P. Nowicki, D. Duval, H. Poignet, B. Scatton, Eur. J. Pharmac. 204, 339 (1991)). Mechanisms proposed for NO neurotoxicity as well as tumoricidal and bactericidal actions include mono-ADP-ribosylation and S-nitrosylation of glyceraldehyde-3-phosphate dehydrogenase (J. Zhang and S. H. Snyder, Proc. Natl. Acad. Sci. U.S.A. 89, 9382 (1992); A. Y. Kots et al., FEBS Lett. 300, 9 (1992); S. Dimmeler, F. Lottspeich, B. Brune, J. Biol. Chem. 267, 16771 (1992); L. Molina y Vedia et al., J. Biol. Chem. 267, 24929 (1992)), inhibition of mitochondrial enzymes such as cis-aconitase (J. -C. Drapier and J. B. Hibbs, Jr., J. Clin. Invest. 78, 790 (1986)), inhibition of the mitochondrial electron transport chain (Nathan and Hibbs, supra), inhibition of ribonucleotide reductase (Lepoivre, B. Chenais, A. Yapo, G. Lemaire, J. Biol. Chem. 265, 14143 (1990); N. S. Kwon, D. J. Stuehr, C. F. Nathan, J. Exp. Med. 174, 761 (1991)), and DNA damage (D. A. Wink et al., Science 254, 1001 (1991); T. Nguyen et al., Proc. Natl. Acad. Sci. U.S.A. 89, 3030 (1992)). DNA damage activates poly(ADP-ribose) synthetase (PARS, EC 2.4.2.30) (G. de Murcia, J. Menissier-de Murcia, V. Schreiber, BioEssays 13,455 (1991); J. E. Cleaver and W. F. Morgan, Mutation Res. 257, 1 (1991); J. C. Gaal, K. R. Smith, C. K. Pearson, Trends in Biological Sciences 12, 129 (1987); N. A. Berger, Rad. Res. 101, 4 (1985)). PARS is a nuclear enzyme which, upon activation by DNA strand breaks, adds up to 100 ADP-ribose units to nuclear proteins such as histones and PARS itself.

There is a continuing need in the art for effective methods of preventing, treating or ameliorating diseases caused by NMDA neurotoxicity, such as vascular stroke, Alzheimer's disease, Huntington's disease, and Parkinson's disease.

SUMMARY OF THE INVENTION

It is an object of the invention to provide a method of treating diseases caused by NMDA neurotoxicity.

It is another object of the invention to provide a method of treating vascular stroke.

Another object of the invention is to provide a method of treating a neurodegenerative disease, such as Huntington's disease, Alzheimer's disease and Parkinson's disease.

It is still another object of the invention to provide pharmaceutical formulations for treating neurodegenerative diseases and vascular stroke damage.

These and other objects of the invention are provided by one or more of the embodiments described below.

In one embodiment of the invention, a method of preventing or treating diseases caused by NMDA neurotoxicity is provided, which method comprises administering to a mammal in need thereof a therapeutically effective amount of a poly(ADP-ribose) synthetase inhibitor.

In another embodiment of the invention, a method of preventing or treating vascular stroke damage in a mammal, in particular a human patient, is provided, which comprises administering a therapeutically effective amount of a poly (ADP-ribose) synthetase inhibitor.

In still another embodiment of the invention, a method of treating a mammal for a neurodegenerative disease caused by NMDA neurotoxicity, in particular preventing or treating a neurodegenerative disease such as Huntington's disease, Alzheimer's disease and Parkinson's disease in a human patient, is provided, which method comprises administering a therapeutically effective amount of a poly(ADP-ribose) synthetase inhibitor.

In yet another embodiment of the invention, a pharmaceutically acceptable formulation is provided which comprises an inhibitor of poly(ADP-ribose) synthetase in a pharmaceutically acceptable vehicle.

Thus the present invention provides the art with methods and formulations for treating neurological damage due to neurodegenerative diseases and vascular stroke.

Data are the means ±SEM (n>8). Each data point represents 4,000–12,000 neurons counted (21). *$p \leqq 0.01$, Student's t-test.

Figure 3:
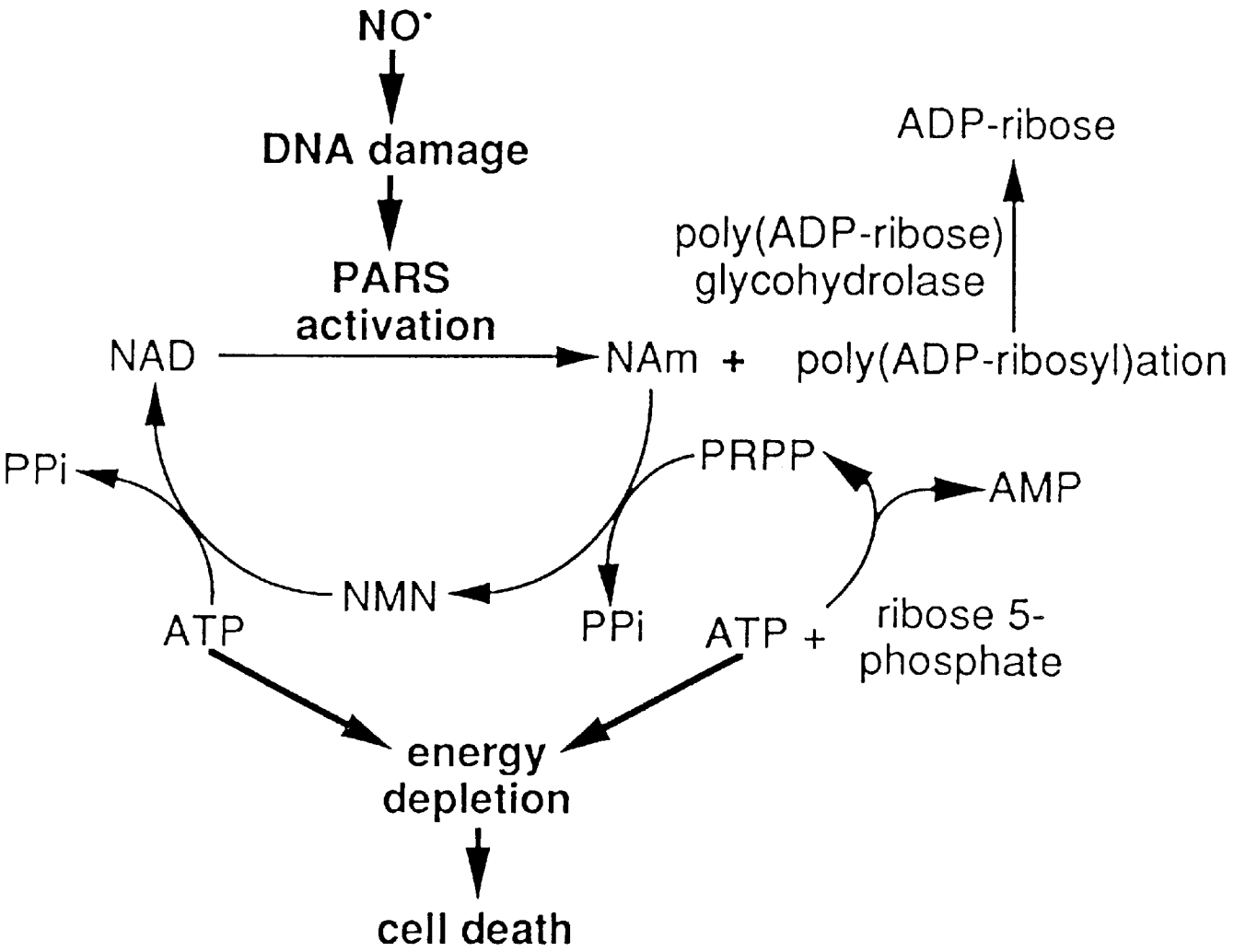

FIG. 3. A Model of NO-mediated Cytotoxicity. NO damaged DNA activates PARS which depletes NAD by poly-ADP-ribosylating neuclear proteins. Poly(ADP-ribose) is rapidly degraded by poly(ADP-ribose) glycohydrolase. The futile cycle continues during the prolonged PARS activation. It takes an equivalent of four ATP's to resynthesize NAD from nicotinamide (NAm) via nicotinamide mononucleotide (NMN), a reaction that requires phosphoribosyl pyrophosphate (PRPP) and ATP.

DETAILED DESCRIPTION OF THE INVENTION

It is a discovery of the present invention that NO activates PARS in association with damage to DNA. PARS activation can kill cells by consuming β-nicotinamide adenine dinucleotide, the source of ADP-ribose, and ATP. Moreover, PARS inhibitors prevent NMDA neurotoxicity with relative potencies paralleling their enzyme inhibitory actions.

Our observation that NO activates PARS fits with other studies indicating that NO damages DNA (D. A. Wink et al., Science 254, 1001 (1991); T. Nguyen et al., Proc. Natl. Acad. Sci. U.S.A. 89, 3030 (1992)). The protection against NMDA neurotoxicity provided by PARS inhibitors appears to reflect PARS inhibition, as the relative potencies of these drugs in blocking neurotoxicity parallel their activities as PARS inhibitors.

The ability of PARS inhibition to provide substantial protection against NMDA neurotoxicity, implicates DNA damage in neuronal killing. PARS activation rapidly leads to energy depletion. For each ADP-ribose unit transferred by PARS, one molecule of NAD is consumed and an equivalent of four molecules of ATP are required to regenerate NAD from nicotinamide, PARS, whose density is up to one enzyme per 10–20 nucleosomes, can be activated 10–20 fold by DNA damage; PARS transfers 50–100 ADP-ribose moieties to each acceptor site of target proteins and its over-activation by substantial DNA damage can markedly deplete cells of NAD and ATP (J. C. Gaal, K. R. Smith, C. K. Pearson, Trends in Biological Sciences 12, 129 (1987); N. A. Berger, Rad. Res. 101, 4 (1985)). Neurotoxicity is similarly associated with a change in the NADH/NAD redox state and energy depletion. (See, for example, O. H. Lowry et al., J. Biol. Chem. 239, 18 (1964); D. Uematsu et al., Brain Research 482, 129 (1989); but also see K. M. Raley and P. Lipton, Neurosci. Lett. 110, 118 (1990)). The protection against NMDA neurotoxicity afforded by PARS inhibition supports a mechanism of cell death in which DNA damage overwhelms repair mechanisms leading to energy depletion by activation of PARS (FIG. 3).

Two major effects of glutamate neurotoxicity suggested to participate in neuronal killing are the formation of free radicals and energy depletion (B. Meldrum and J. Garthwaite, Trends Pharmacol. Sci. 11, 379 (1990)). Our findings indicate that both participate, with NO, a free radical, triggering DNA damage, which in turn activates PARS, ultimately depleting energy sources from the cell. This mechanism of cell death might also account for the tumoricidal effects of NO formed by macrophages, which fits with observations that 3-aminobenzamide protects pancreatic islet cells from macrophage cytotoxicity (B. Kallman et al., Life Sci. 51, 671 (1992)).

Poly(ADP-ribose) synthetase inhibitors may be used to prevent, treat, arrest, or ameliorate the progression of any disease condition caused by NMDA neurotoxicity. Such conditions include vascular strokes and neurodegenerative diseases, such as Alzheimer's, Huntington's and Parkinson's diseases, as well as other disease states. For example, following the symptoms of a stroke, a patient is administered a poly(ADP-ribose) synthetase inhibitor to block damage to the brain. Patients with symptoms of Alzheimer's or Huntington's disease are treated with poly(ADP-ribose) synthatase inhibitors to halt the progression of the disease. The symptoms of these disease states are known by one skilled in this art.

Inhibitors of poly(ADP-ribose) synthetase are compounds which compete for the substrate binding site of poly(ADP-ribose) synthetase or other sites on the enzyme, and include both reversible and irreversible inhibitors. The present invention contemplates the use of any physiologically acceptable inhibitor which inhibits poly(ADP-ribose) synthetase activity. The effectiveness of a compound, and its relative potency as a poly(ADP-ribose) synthetase inhibitor, can be tested and routinely determined by measuring inhibition of poly(ADP-ribose) synthetase activity. Poly(ADP-ribose) synthetase activity can be assayed according to the method of Schranfstatter, et al., J. Clin. Inves. 77, 1312 (1986).

Both benzamide and 1,5-dihydroxy-isoquinoline, two poly(ADP-ribose) synthetase inhibitors, have been found to prevent neurotoxicity in proportion to their relative potencies as poly(ADP-ribose) synthetase inhibitors. In addition, various benzamide derivatives have been found to have the ability to prevent neurotoxicity in proportion to their relative potencies as poly(ADP-ribose) synthetase inhibitors. These include: 3-aminobenzamide and 4-aminobenzamide. Benzoic acid was found not to have any activity. In addition, novobiocin, an inhibitor of mono(ADP-ribose) synthetase was found not to have any activity in preventing neurotoxicity.

The dosage and length of treatment depends on the disease state being treated. The duration of treatment may be a day, a week or longer and may, as in the case of a chronic progressive illness, such as Alzheimer's, last over the entire lifetime of the patient. The inhibitors are administered in a therapeutically effective amount, a typical human dosage of benzamide ranging from about 0.01 mg/kg of body weight to about 10 mg/kg, in single or divided doses. The dosage will vary depending on the poly(ADP-ribose) synthetase inhibitor being used and its relative potency. Dosage and length of treatment are readily determinable by the skilled practitioner based on the condition and stage of disease.

In therapeutic use, poly(ADP-ribose) synthetase inhibitors may be administered by any route by which drugs are conventionally administered. Such routes of administration include intraperitoneal, intravenous, intramuscular, subcutaneous, intrathecal, intraventricular, as well as oral.

Typical pharmaceutically acceptable preparations for administration include sterile aqueous or nonaqueous solutions, suspensions and emulsions. Examples of non-aqueous solvents are propylene glycol, polyethylene glycol, vegetable oils such as olive oil and injectable organic esters such as ethyl oleate. Aqueous carriers include water alcoholic/aqueous and buffered media. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like. Oral preparations, such as in capsule, tablets, and other form include additives such as cellulose, silica gel and stearic acid.

To be effective therapeutically, a poly(ADP-ribose) synthetase inhibitor desirably should be able to penetrate the blood brain barrier when peripherally administrated. Poly (ADP-ribose) synthetase inhibitors which are unable to penetrate the blood brain barrier can be effectively administered by, for example, an intraventricular route of delivery.

The following examples are provided to exemplify various aspects of the invention and are not intended to limit the scope of the invention.

EXAMPLE 1

This example demonstrates the activation of PARS by NO-treated DNA, as well as the inhibition of such activation by PARS inhibitors.

Figure 1A:
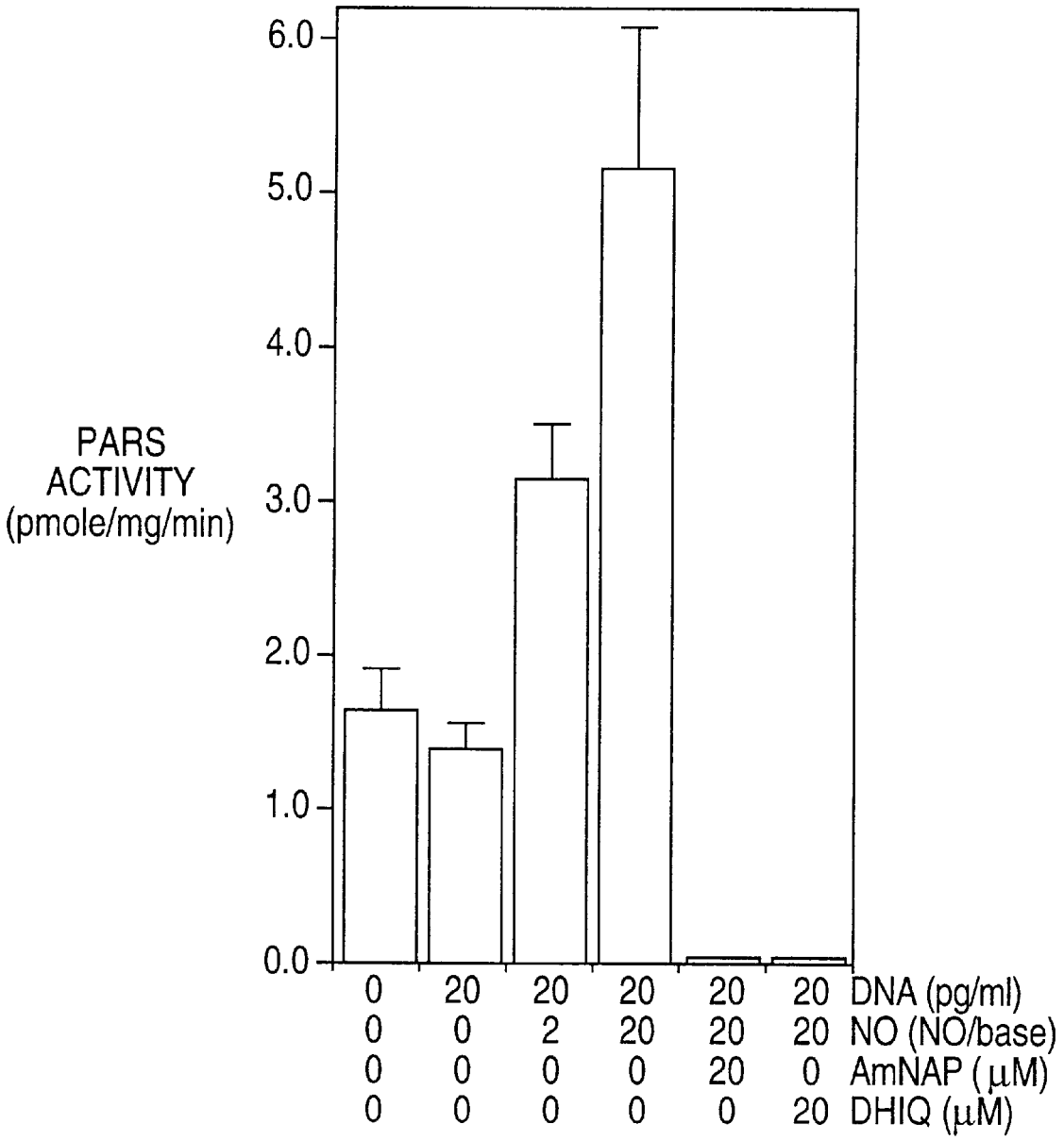
FIG. 1. Activation of PARS by NO-damaged DNA. (A) PARS activity, (means ±S.E.M., n=3), after different treatments. (B) Autoradiography of PARS auto-poly(ADP-ribosyl)ation on 7.5% SDS-PAGE. Abbreviations AmNAP, 4amino-1,8-naphthalimide, DHIQ, 1,5-dihydroxyisoquinoline.
Figure 1B:
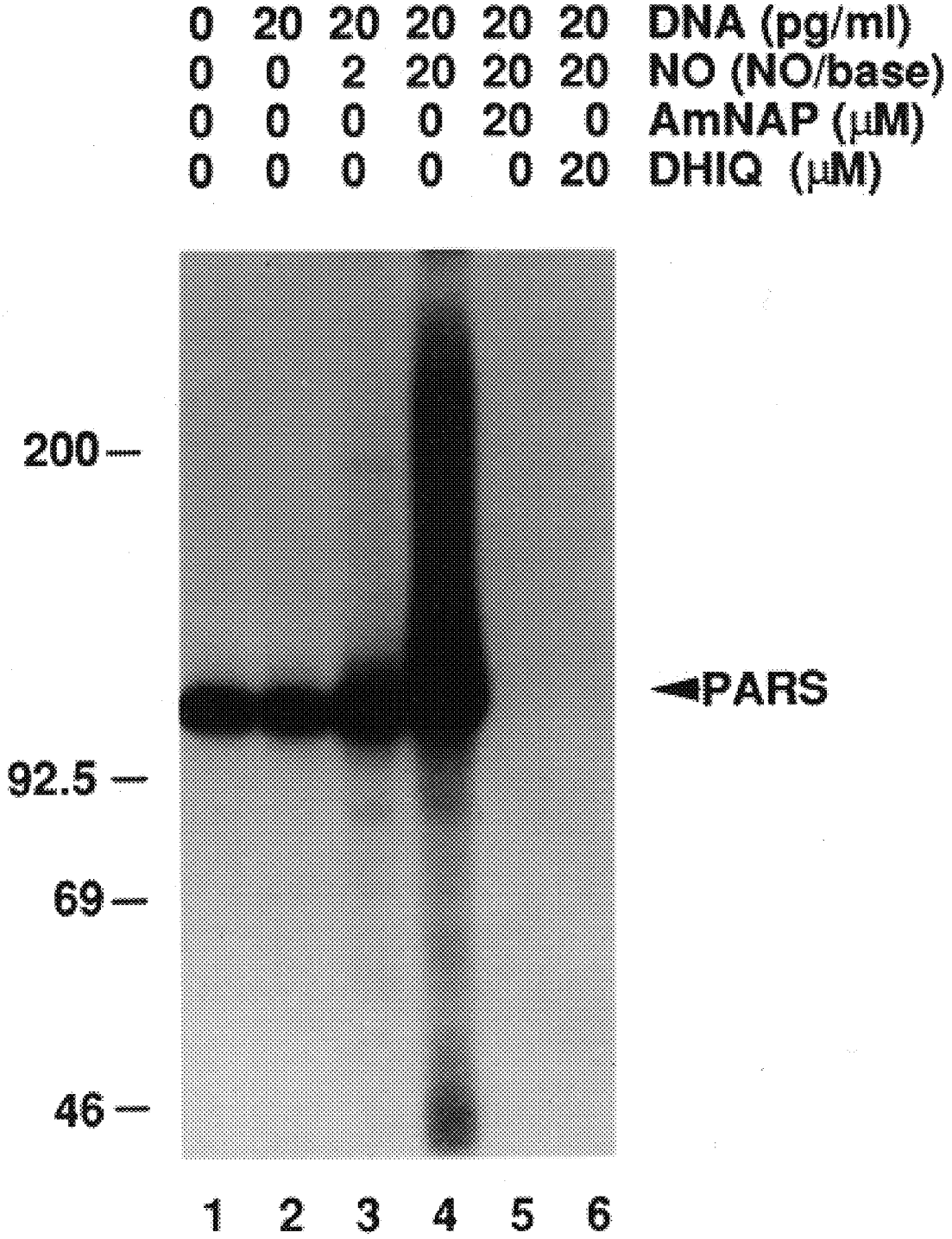

In rat brain nuclear extracts, PARS activity was almost tripled dose-dependently by adding DNA that had been pre-incubated with NO (FIG. 1A). Addition of covalently closed circular DNA by itself had no effect on PARS activity. Both 4amino-1,8-naphthalimide and 1,5-dihydroxyisoquinoline, two potent PARS inhibitors, reduced the activity to <5% of basal levels (FIG. 1A). The major protein ADP-ribosylated in the nuclear extracts was PARS itself (FIG. 1B). Similarly, DNA that had been treated with 3-morpholinosyndnonimine (SIN-1) and sodium nitroprusside (SNP), two NO donors, could stimulate poly (ADP-ribose) synthesis, which was inhibited by benzamide, another PARS inhibitor. SNP and SIN-1 had no effect on PARS by themselves.

Whole brains from 1-day old rats were homogenized in 20% (w/v) buffer A [50 mM Tris-HCl (pH 7.4), 1 mM EDTA, 1 mM DTT, 50 mM NaCl, 0.25M sucrose, 0.2 mM phenylmethylsulfonyl fluoride, 1 $\mu$g/ml each of chymostatin, leupeptin, pepstatin and trypsin inhibitor]. The homogenate was centrifuged at 1000 g for 15 min. The pellet was washed with buffer A and centrifuged again. The washed pellet, termed nuclear fraction, was resuspended in buffer A. PARS activity was assayed according to I. U. Schranfstatter, et al., J. Clin. Inves. 77, 1312 (1986). Each 50 $\mu$l assay mixture contained 10 $\mu$g of the nuclear protein fraction and [adenylate-$^{32}$P] NAD (0.1 mM, 10 Ci/mmole), in the presence or absence of 4-amino-1,8-naphthalimide (20 $\mu$M), 1,5-dihydroxyisoquinoline (20 $\mu$M), benzamide (100 $\mu$M, SNP (1 mM), SIN-1 (1 mM), DNA (0.1 pg, pTrcA, In Vitrogen) and DNA that had been treated with NO gas, SNP or SIN-1. Incubation of DNA with NO gas was according to T. Nguyen et al., Proc. Natl. Acad. Sci. USA 89, 3030 (1992). SNP and SIN-1 treated DNA doubled PARS activity, while both compounds had no effects on PARS by themselves. When [$^{14}$C]NAD's were used in place of [$^{32}$P]NAD in PARS assay, radioactive polymers were only formed from [adenine-$^{14}$C] NAD but not from [carbonyl-$^{14}$C]NAD.

McDonald and Moss recently demonstrated that NO-enhanced modification of GAPDH by NAD involves the transfer of the entire NAD to a thiol group rather than ADP-ribosylation (J. P. Nowicki, D. Duval, H. Poignet, B. Scatton, Eur. J. Pharmac. 204, 339 (1991)). To ensure that the polymer formed from NAD in our study was poly(ADP-ribose), we used both [$^{14}$C-adenine] NAD and [$^{14}$C-nicotinamide] NAD and found radioactivity could only be incorporated into the polymers from the former compound.

EXAMPLE 2

This example demonstrates that PARS inhibitors inhibit the neurotoxicity elicited by NMDA.

Figure 2:
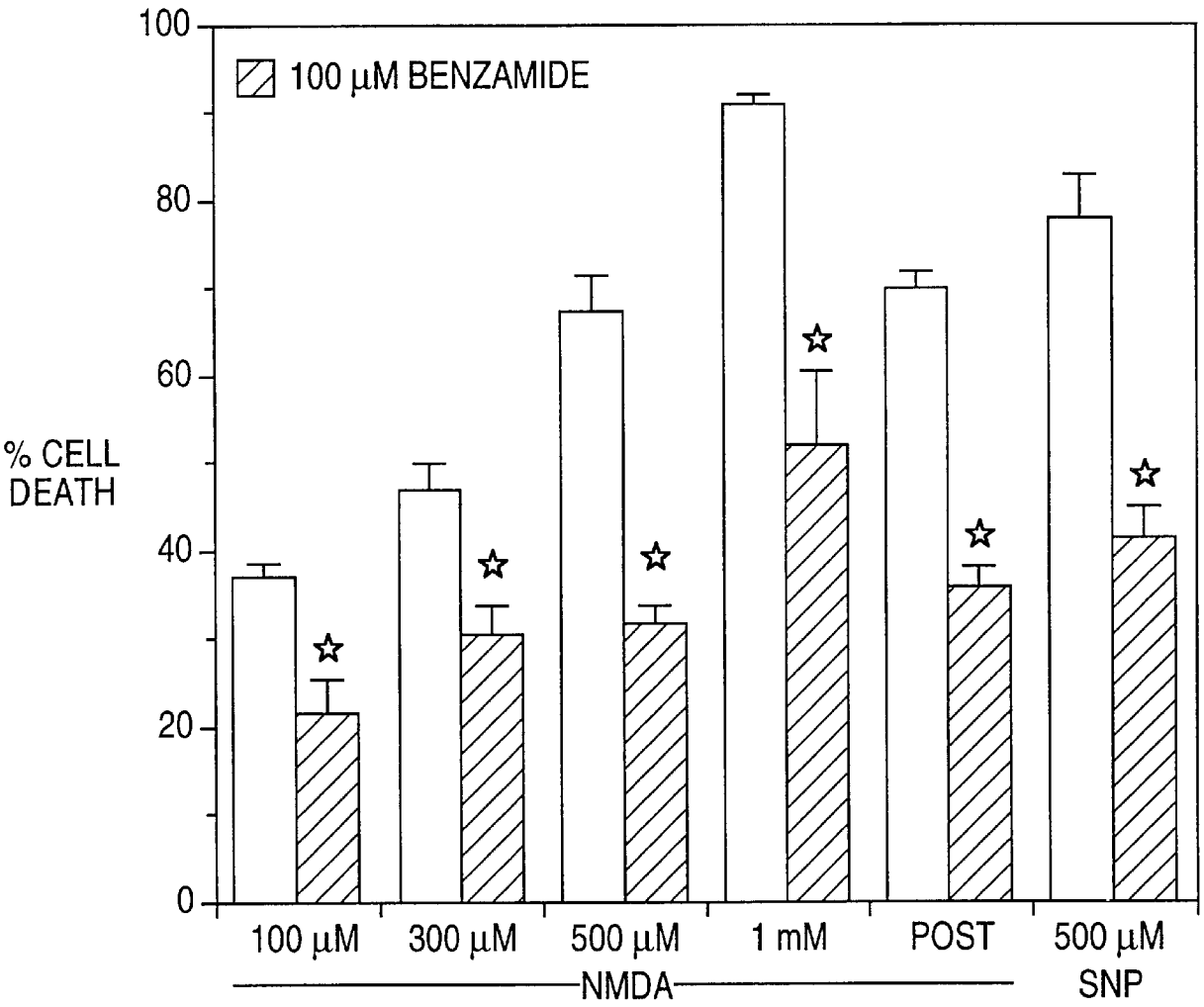
FIG. 2. Inhibition of NMDA and NO mediated Neurotoxicity by PARS Inhibitors. 100 $\mu$M benzamide reduces NMDA, SNP (500 $\mu$M) and SNAP (300 $\mu$M) mediated neurotoxicity.

To determine directly if PARS activation participates in NMDA neurotoxicity, we monitored neurotoxicity elicited by NMDA in cerebral cortical cultures in which NO synthase inhibitors provide marked protection (V. L. Dawson et al., Proc. Natl. Acad. Sci. U.S.A. 88, 6368 (1991); V. L. Dawson et al., J. Neurosci. 13, 2651 (1993)) (FIG. 2). Increasing concentrations of NMDA progressively augment neuronal killing. Benzamide (100 $\mu$M) provided 40–50% protection at all NMDA concentrations examined. At 50 $\mu$M benzamide, no significant protection was detected, while 500 $\mu$M benzamide provided about 30% greater protection than at 100 $\mu$M (Table 1A). NO did not interact with benzamide.

To test whether NO interacts directly with benzamide, we incubated benzamide (1 mM) with SNP (1 mM) for five days at 25° C., and analyzed it by HPLC on a $C_{18}$ column. SNP-treated benzamide was 100% recovered at the same elution time point with the same UV spectrum as that of unreated benzamide. When SNP-treated benzamide and benzamide were mixed and analyzed only one peak was observed.

A variety of benzamide derivatives exist with differing potencies as PARS inhibitors. In the family of benzamide and its derivatives, benzamide is the most active, 3-aminobenzamide is about half as potent, 4-aminobenzamide is 50–100 fold weaker than benzamide and benzoic acid is inactive (The $IC_{50}$ for benzamide in inhibiting PARS in vitro is 22 $\mu$M [M. Banasik, H. Komura, M. Shimoyama, K. Ueda, J. Biol. Chem. 267, 1569 (1992)]. In intact cells a higher value would be anticipated as benzamide would be competing with millimolar endogenous levels of NAD [R. McNerney et al., Biochim. Biophys. Acta 1009, 185 (1989)].

Benzamide provided the greatest degree of protection, with 3-aminobenzamide exerting somewhat less protection against NMDA neurotoxicity, while 4-aminobenzamide and benzoic acid were inactive (Table 1 ). A structurally unrelated PARS inhibitor, 1,5-dihydroxyisoquinoline (10 $\mu$M), was also neuroprotective against NMDA neurotoxicity (Table 1A). The absolute as well as the relative potencies of the benzamide derivatives and 1,5-dihydroxyisoquinoline in blocking NMDA toxicity correspond with their potencies as PARS inhibitors. It is unlikely that the PARS inhibitors could prevent NMDA neurotoxicity through inhibition of mono(ADP-ribose) synthetase as their $IC_{50}$'s for mono (ADP-ribose) synthetase inhibition are at least 100 times greater than their $IC_{50}$'s as PARS inhibitors. Furthermore, novobiocin (1 mM) a relatively selective mono(ADP-ribose) synthetase inhibitor was ineffective against NMDA neurotoxicity (Table 1A).

Brief (5 rain) NMDA exposure initiates "delayed neurotoxicity" in which poorly characterized irreversible processes ultimately lead to calcium overload and cell death (R. D. Randall and S. A. Thayer, J. Neurosci. 12, 1882 (1992); D. W. Choi, Neuron 1, 623 (1988); D. W. Choi, J. Neurosci. 10, 2493 (1990)). In most experiments benzamide was added prior to the NMDA and during NMDA exposure (FIG. 2, Table 1A). However, in some experiments we have added benzamide up to 1 hr after NMDA exposure and observed similar protection (Table 1B).

TABLE 1

| Treatment | % Cell Death (+ S.E.M.) |
|---|---|
| A. PARS Inhibitors Protect Against NMDA Neurotoxicity | |
| 500 $\mu$M NMDA | 57.1 ± 4.7 |
| +50 $\mu$M Benzamide | 60.1 ± 12.1 |
| +100 $\mu$M Benzamide | 39.5 ± 5.0* |
| +500 $\mu$M Benazmide | 21.9 ± 4.1* |
| +100 $\mu$M 3-aminobenzamide | 45.9 ± 5.1* |
| +100 $\mu$M 4-aminobenzamide | 55.8 ± 7.6 |
| +1 mM Benzoic Acid | 58.9 ± 5.7 |
| +10 $\mu$M 1.5 dihydroxyisoquinoline | 39.0 ± 4.5* |
| +1 mM Novobiocin | 62.4 ± 8.9 |
| B. PARS Inhibitors Rescue Neurons From NMDA Neurotoxicity | |
| 500 $\mu$M NMDA | 74.7 ± 7.8 |
| +100 $\mu$M Benzamide | |
| 5 min | 35.6 ± 8.7* |
| 30 min | 40.4 ± 5.6* |
| 1 hour | 43.4 ± 3.9* |

Table 1A, PARS inhibitors were applied 30 min before and during NMDA application. In Table 1B, PARS inhibitors were applied after NMDA administration at the indicated times for 20 to 24 hr. Data are the means ±SEM (n≧8). Each data point represents 4,000–12,000 neurons counted. *p≦0.001 Student's t-test.

Primary neuronal cultures from cortex were prepared from fetal Sprague-Dawley rats, gestation day 13–14. Mature neurons (grater than 21 days in culture) were used in all experiments.

Neurotoxicity was determined by exposing the neurons to the various test solutions as previously described (Dawson, supra). NADA, SNP or SNAP were applied to the cells for 5 min, then the cells were washed and replaced with MEM, 21 mM glucose overnight in the incubator. Twenty to 24 hr after exposure to test solutions, the neurons were exposed to 0.4% trypan blue in CSS to stain the residue of non-viable cells and to assess toxicity. Viable and non-viable cells were counted. At least two separate experiments utilizing four separate wells were performed for each data point shown. Significant overall values were obtained by using a one-way, between groups analysis of variance. Specific comparisons on all possible pair combinations were made with the Student's t-test for independent means.

EXAMPLE 3

This example demonstrates that NO elicits neurotoxicity by activation of PARS.

To ascertain whether NO itself elicits neurotoxicity by activation of PARS, we administered the NO releasers SNP and S-nitroso-N-acetylpenicillamine (SNAP). Benzamide (100 μM) reduced SNP and SNAP neurotoxicity by 45% to 50% (FIG. 2). Benzamide does not inhibit NOS. In human kidney 293 cells stably transfected with the cDNA of brain. NOS, stimulated levels of nitrite, an indirect measure of NO production, were not affected by 100 μM benzamide, but were abolished by nitroarginic. This experiment also confirms that benzamide did not interact with NO.

Nitrite formation in a human kidney 293 cell line stably transfected with the cDNA for brain NOS was measured in response to A23187 (10 μM) as described (D. S. Bredt, C. D. Ferris and S. H. Snyder, J. Biol. Chem. 267, 10976 (1992). A23187 (10 μM) elicited the formation of 17.1±2.1 μM nitrite in 2 hr. Benzamide (100 μM) did not prevent the formation of nitrite (15.9±3.8 μM nitrite) and 100 μM nitroarginine diminished nitrite formation to 3.9±1.6 μM nitrite (n=3).

We claim:

1. A method of treating a disease condition caused by [NMDA] *glutamate* neurotoxicity in a mammal comprising:

administering to a mammal which demonstrates symptoms of a disease condition caused by [NMDA] *glutamate* neurotoxicity a therapeutically effective amount of an inhibitor of poly (ADP-ribose) synthetase.

2. The method of claim 1 wherein said inhibitor is administered intravenously, intraperitoneally, intramuscularly, intraventricularly, or orally.

3. The method of claim 2 wherein said inhibitor is benzamide.

4. The method of claim 1 wherein said inhibitor is benzamide.

[5. The method of claim 1 wherein said inhibitor is a benzamide derivative selected from the group consisting of 3-aminobenzamide and 4-aminobenzamide.]

6. The method of claim [5] *1* wherein said inhibitor is 3-aminobenzamide.

[7. The method of claim 5 wherein said inhibitor is 4-aminobenzamide.]

8. The method of claim 1 wherein said inhibitor is 1,5-dihydroxy-isoquinoline.

9. The method of claim 1 wherein said disease is vascular stroke.

10. The method of claim 1 wherein said disease is a neurodegenerative disease.

11. A pharmaceutical formulation comprising *a therapeutically effective amount of* an inhibitor of poly(ADP-ribose) synthetase *containing a single or divided dose having a potency equivalent to about 10 mg/kg of body weight or less of benzamide* in a pharmaceutically acceptable vehicle.

12. The pharmaceutical formulation of claim 11 wherein said inhibitor is benzamide.

[13. The pharmaceutical formulation of claim 11 wherein said inhibitor is a benzamide derivative selected from the group consisting of 3-aminobenzamide and 4-amino benzamide.]

14. The pharmaceutical formulation of claim [13] *11* wherein said inhibitor is 3-aminobenzamide.

[15. The pharmaceutical formulation of claim 13 wherein said inhibitor is 4-aminobenzamide.]

16. The pharmaceutical formulation of claim 11 wherein said inhibitor is 1,5-dihydroxy-isoquinoline.

17. The pharmaceutical formulation of claim 11 wherein said inhibitor has an $IC_{50}$ for inhibiting poly(ADP-ribose) synthetase in vitro of at least *as potent as* 22 μM.

18. The pharmaceutical formulation of claim 11 wherein said inhibitor has an $IC_{50}$ for inhibiting poly(ADP-ribose) synthetase in vitro of at least *as potent as* 33 μM.

19. The pharmaceutical formulation of claim 11 wherein said formulation is a capsule or tablet containing a single or divided dose of said inhibitor, wherein said dose is sufficient to treat [NMDA] *glutamate* neurotoxicity.

20. The pharmaceutical formulation of claim 11 which is a sterile solution, suspension or emulsion, in a single or divided dose, for administration to a mammal which demonstrates symptoms of a disease condition caused by [NMDA] *glutamate* neurotoxicity.

*21. The pharmaceutical formulation of claim 11 wherein said formulation is a capsule or tablet containing a single or divided dose of said inhibitor, wherein said dose is sufficient to treat glutamate neurotoxicity mediated through NMDA receptors.*

*22. The pharmaceutical formulation of claim 11 which is a sterile solution, suspension or emulsion, in a single or divided dose, for administration to a mammal which demonstrates symptoms of a disease condition caused by glutamate neurotoxicity mediated through NMDA receptors.*

*23. A method of claim 1 wherein said therapeutically effective amount of an inhibitor of poly (ADP-ribose) synthetase is in the form of a single or divided dose having a potency equivalent to about 10 mg/kg of body weight or less of benzamide.*

*24. A method of treating a disease condition caused by glutamate neurotoxicity in a mammal comprising:*

*administering to a mammal which demonstrates symptoms of a disease condition caused by glutamate neurotoxicity mediated through NMDA receptors a therapeutically effective amount of an inhibitor of poly (ADP-ribose) synthetase.*

*25. The method of claim 24 wherein said inhibitor is administered intravenously, intraperitoneally, intramuscularly, intraventricularly, or orally.*

*26. The method of claim 24 wherein said inhibitor is benzamide.*

*27. The method of claim 25 wherein said inhibitor is benzamide.*

*28. The method of claim 24 wherein said inhibitor is 3-aminobenzamide.*

*29. The method of claim 24 wherein said inhibitor is 1,5-dihydroxy-isoquinoline.*

*30. The method of claim 24 wherein said disease is vascular stroke.*

*31. The method of claim 24 wherein said disease is a neurodegenerative disease.*

*32. A method of claim 24 wherein said therapeutically effective amount of an inhibitor of poly (ADP-ribose) synthetase is in the form of a single or divided dose having a potency equivalent to about 10 mg/kg of body weight or less of benzamide.*

* * * * *